| United States Patent [19]
Kamiya et al.

[11] Patent Number: 4,859,696
[45] Date of Patent: Aug. 22, 1989

[54] PRECUTANEOUS ABSORPTION ACCELERATOR AND PREPARATION CONTAINING SAME

[75] Inventors: Tetsuro Kamiya; Takeshi Inoue; Hidenori Yorozu; Yasuteru Eguchi; Kaoru Tsujii, all of Tochigi, Japan

[73] Assignee: Kao Corporation, Tokyo, Japan

[21] Appl. No.: 227,777

[22] Filed: Aug. 3, 1988

Related U.S. Application Data

[63] Continuation of Ser. No. 47,513, May 6, 1987, abandoned, which is a continuation of Ser. No. 726,320, Apr. 23, 1985, abandoned.

[30] Foreign Application Priority Data

Apr. 23, 1984 [JP] Japan ................................. 59-82464

[51] Int. Cl.$^4$ .............................................. A61K 31/405
[52] U.S. Cl. ...................... 514/420; 514/772; 514/969; 514/946; 514/947; 424/449; 424/45; 568/678; 568/679; 568/680; 104/304
[58] Field of Search ...................... 568/678, 679, 680; 514/772, 420, 969, 946, 947; 424/449, 45; 604/304

[56] References Cited

U.S. PATENT DOCUMENTS

| | | |
|---|---|---|
| 3,666,671 | 5/1972 | Kalopissis et al. . |
| 4,309,414 | 1/1982 | Inagi et al. . |
| 4,339,447 | 7/1982 | Boguth et al. . |
| 4,393,057 | 7/1983 | Boguth et al. . |
| 4,393,073 | 7/1983 | Boguth et al. . |
| 4,440,777 | 3/1984 | Lupan . |
| 4,543,258 | 9/1985 | Urata et al. . |
| 4,746,509 | 5/1988 | Haggiage et al. ................... 424/449 |

FOREIGN PATENT DOCUMENTS

| | | |
|---|---|---|
| 1142969 | 3/1983 | Canada . |
| 35132 | 9/1981 | European Pat. Off. . |
| 0035132 | 9/1981 | European Pat. Off. . |
| 71019 | 2/1983 | European Pat. Off. . |
| 1539625 | 1/1979 | United Kingdom . |
| 2069334 | 8/1981 | United Kingdom . |

OTHER PUBLICATIONS

Holford et al., "Transdermal Systems in Principle and Pratice," Current Therapeutics, Jan. 1984, Leading Article.
Chemical Abstracts 97:203091f, vol. 97, p. 323, (1982).
Chemical Abstracts, vol. 97, 1982, (p. 323-203091f).

*Primary Examiner*—Howard T. Mars
*Attorney, Agent, or Firm*—Birch, Stewart, Kolasch & Birch

[57] ABSTRACT

A percutaneous absorption accelerator and a precutaneous absorbent preparation containing the same and, more particularly, a percutaneous absorption accelerator containing ether derivatives of specific glycerols or polyglycerols and alcohols as effective components and a percutaneous absorbent preparation containing the percutaneous absorption accelerators and pharmaceutically effective components.

8 Claims, 1 Drawing Sheet

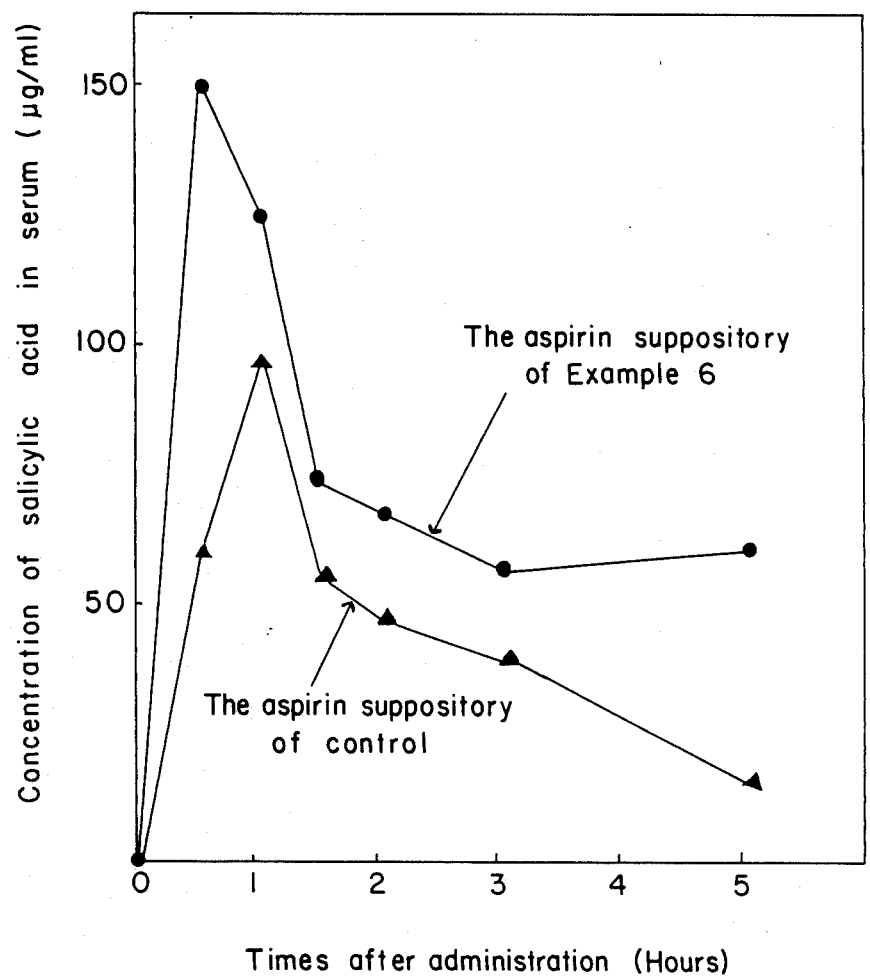

PRECUTANEOUS ABSORPTION ACCELERATOR AND PREPARATION CONTAINING SAME

This application is a continuation of Ser. No. 047,513 filed May 6, 1987 now abandoned which is a continuation of Ser. No. 726,320 filed Apr. 23, 1985 now abandoned.

BACKGROUND OF THE INVENTION

The present invention relates to a percutaneous absorption accelerator and a percutaneous absorbent preparation containing the same, and more particularly, to a percutaneous absorption accelerator containing ether derivatives of specific glycerols or polyglycerols and alcohols as the active ingredients and percutaneous absorbent accelerators and pharmaceutically effective components.

As methods for administration of drugs, oral administration, rectal administration, intracutaneous administration, and so forth have been generally adopted. Among these, oral administration has been widely employed. However, in the case of oral administration, certain difficulties have been encountered due to side effects such as gastrointestinal disturbances, anorexia, vomitting, and abdominal pain. In addition it is necessary in most cases to administer large quantities of these drugs. In recent years, preparations for percutaneous administration have been developed, some have been for, commercial use, in hopes that the side effects would be minimized and the desired pharmacological effects would occur more safely. In many cases, however, percutaneo absorbability of pharmaceutically effective components in such preparations are unsatisfactory and the purposes have been satisfactorily achieved only with difficulty. Namely, skin and its keratin layer (which constitutes the outermost layer) functions physiologically and acts as a protective wall against permeation of substances into the body. In many cases, it is difficult for a base alone, used for conventional topical agents, to attain percutaneous absorption sufficient for the pharmaceutically components formulated therein to be effective. For this reason, a device is necessary to control the permeability of drugs through the keratin layer of the skin and enhance the percutaneous absorption of drugs.

In addition, for accelerating absorption of pharmacologically active substances from the mucous portions of the human body, such as the mucous membrane of the eye, nasal mucous membrane, bucal mucous membrane, vaginal mucous membrane, rectal mucous membrane, improvement of the preparation form, improvement of bases, formulation of compounds having an absorption acceleration effect, and the like have been made. Among them, the improvement of the preparation form and the improvement of bases are possible to a certain extent; however, epochmaking improvement is not expected and the target of research has been focused on the search for and application of compounds having an absorption accelerating effect.

For such purposes, it has generally been known to formulate a so called percutaneous absorption accelerator in a base. As such absorption accelerators, there are known dimethyl sulfoxide; amide compounds such as dimethyl acetamide, dimethylformamide, and N,N-diethyl-m-toluamide, azacycloalkan-2-one derivatives, such as 1-dodecylazacyclo-heptan-2-one; esters of alcohol and carboxylic acids, such as isopropyl myristate, isopropyl palmitate, diethyl sebacate, and diisopropyl adipate; and crotonyl-N-ethyl-o-toluidine. However, these absorption accelerators have been found to be unsatisfactory in their absorption accelerating effect and, in many cases, practical pharmacological effects cannot be obtained. In addition, these pharmacological effects cannot be obtained. Moreover, these absorption accelerators involve problems in practical use because the absorption accelerators themselves show irritation to the skin and corrode synthetic resins due to their property as potent solvents to dissolve irritative substances, and sensitized substances out of containers for drugs, clothes, and accessories, so that general adaptation and use are restricted.

SUMMARY OF THE INVENTION

Therefore, in accordance with the present invention it has been found that by formulating specific ether derivatives of glycerols or polyglycerols as percutaneous absorption accelerators in a base, percutaneous absorption of pharmaceutically effective components can be markedly increased and the pharmacological effects of the pharmaceutically effective components can be demonstrated effectively and safely.

DETAILED DESCRIPTION

Namely, the present invention provides percutaneous absorption accelerators comprising ether compounds of glycerols or polyglycerols and alcohols (hereafter simply referred to as "ether derivatives") as essential components and, percutaneous absorbent preparations containing pharmaceutically effective components and the percutaneous absorption accelerators. The term percutaneous absorption in the present invention means the absorption through a mucosal portion of the human body, such as the mucous membrane of the eye, nasal mucous membrane, buccal mucous membrane, vaginal mucous membrane, rectal mucous membrane, and the like in addition to the topical percutaneous absorption through the keratin layer of the skin.

The ether derivatives used in the present invention are obtained by reacting alcohols with glycerols or polyglycerols derived therefrom in a conventional manner. Specific examples of alcohols which are used include straight chain type aliphatic alcohols, such as methyl alcohol, ethyl alcohol, propyl alcohol, butyl alcohol, octyl alcohol, decyl alcohol, dodecyl alcohol, hexadecyl alcohol, octadecyl alcohol, and octadecanyl (oleyl) alcohol; branched type aliphatic primary alcohols, such as isopropyl alcohol, isobutyl alcohol, 2-ethylhexyl alcohol, 2-heptylundecyl alcohol, 2-(1,3,3-trimethylbutyl) octyl alcohol, 2-decyltetradecyl alcohol, 2-dodecylhexadecyl alcohol, 2-tetradecyloctadecyl alcohol, 5,7,7-trimethyl-2-(1,3,3-trimethylbutyl)octyl alcohol and methyl-branced isostearyl alcohols represented by the following formula:

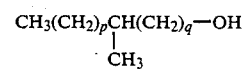

wherein p represents an integer of 4 to 10; and q represents an integer of 5 to 11, and p+q represents 11 to 17 and has a distribution which is optimum when p is 17 and q is 18; secondary alcohols, such as sec-octyl alcohol, sec-decyl alcohol, and sec-dodecyl alcohol; tertiary alcohols, such t-octyl alcohol, and t-dodecyl alcohol; alicyclic alcohols such as cyclohexyl alcohol, and cyclopentyl alcohol; alkylphenols, such as octylphenol, and nonylphenol.

Of the other derivatives used in the present invention preferred are those represented by the following formula (I) or (II):

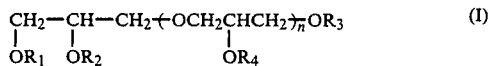 (I)

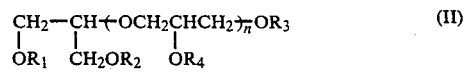 (II)

wherein $R_1$, $R_2$, $R_3$ and $R_4$ (n numbers of $R_4$ may be the same or different) each represents a hydrogen, a saturated or unsaturated straight or branched aliphatic hydrocarbon group or aromatic hydrocarbon group having 1 to 24 carbon atoms, provided that $R_1$, $R_2$, $R_3$ and $R_4$ (n times repeated) are not all hydrogen; and n represents an integer of 0 to 60.

In the ether derivatives represented by the formula (I) or (II), it is preferred that $R_1$ to $R_4$ each be an aliphatic hydrocarbon having 1 to 18 carbon atoms and the total carbon atoms of $R_1$ to $R_4$ be 4 to 36, preferably 8 to 12. Further, it is preferred that n be a number of 0 to 60. Particularly preferred are those wherein n is 0 to 20, and preferably 0 to 10. A more preferred combination of $R_1$ to $R_4$ and n is the combination wherein n is 0 or 1 and the total carbon atoms of $R_1$ to $R_4$ are 4 to 36, particularly the combination in which n is 1 and the total carbon atoms of $R_1$ to $R_4$ is 8 to 22.

Of the ether derivatives (I) or (II), preferred examples include straight chain primary alkyl glycerols, such as 1-O-n-octylglycerol, 1-O-n-decylglycerol, 1-O-n-dodecylglycerol, 1-O-n-tetradecylglycerol, 1-O-n-hexadecylglycerol, 1-O-n-octadecylglycerol, and 1-O-n-octadecenylglycerol branched chain primary alkylglycerols, such as 1-O-2-ethylhexylglycerol, 1-O-2-hexyldecylglycerol, 1-O-2-heptylundecylglycerol, 1-O-2-octyldodecylglycerol, 1-O-2-(1,3,3-trimethylbutyl)octylglycerol, 1-O-5,7,7-trimethyl-2-(1,3,3-trimethylbutyl)octylglycerol, and 1-O methyl-branched isostearylglycerols;

secondary alkylglycerols, such as 1-O-sec-octylglycerol, 1-O-sec-decylglycerol, and 1-O-sec-dodecylglycerol; 1-O-alkylglycerols, such as 1-O-t-octylglycerol, 1-O-t-dodecylglycerol; 1-O-alkyl-3-O-2',3'-dihydroxypropylglycerols such as 1-O-n-octyl-3-O-2',3'-dihydroxypropylglycerol, 1-O-n-dodecyl-3-O-2',3'-dihydroxypropylglycerol, 1-O-n-tetradecyl-3-O-2',3'-dihydroxypropylglycerol, 1-O-n-hexadecyl-3-O-2',3'-dihydroxypropylglycerol, 1-O-n-octadecyl-3-O-2',3'-di-hydroxypropylglycerol, 1-O-n-octadecenyl-3-O-2',3'-dihydroxypropylglycerol, and 1-O-methyl-branched isostearyl-3-O-2',3'-dihydroxypropylglycerol;
1,2-di-O-alkyl-3-O-2',3'-dihydroxypropylglycerols,
such as 1-O-n-octyl-2-O-methyl-3-O-2',3'-dihydroxypropylglycerol, 1-O-n-dodecyl-2-O-methyl-3-O-2',3'-dihydroxypropylglycerol, 1-O-n-dodecyl-2-O-n-butyl-3-O-2',3'-dihydroxypropylglycerol, 1-O-n-dodecyl-2-O-n-octyl-3-O-2',3'-dihydroxypropylglycerol, 1-O-n-tetradecyl-2-O-methyl-3-O-2',3'-dihydroxypropylglycerol, 1-O-n-hexadecyl-2-O-methyl-3-O-2',3'-dihydroxypropylglycerol, 1-O-n-octadecyl-2-O-methyl-3-O-2',3'-dihydroxypropylglycerol, 1-O-n-octadecenyl-2-O-methyl-3-O-2',3'-dihydroxypropylglycerol, 1-O-n-octadecenyl-2-O-n-butyl-3-O-2',3'-dihydroxypropylglycerol, 1-O-methyl-branched isostearyl-2-O-methyl-3-O-2',3'-dihydroxypropylglycerol, and 1-O-methyl-branched isostearyl-2-O-n-octyl-3-O-2',3'-dihydroxypropylglycerol; 1,3-di-O-alkyl-2-O-2',3'-dihydroxypropylglycerols, such as 1-O-n-octyl-3-O-methyl-2-O-2',3'-dihydroxypropylglycerol, 1-O-n-do-decyl-3-O-methyl-2-O-2',3'-dihydroxypropylglycerol, 1-O-n-dodecyl-3-O-n-butyl-2-O-2',3'-dihydroxypropylglycerol, 1-O-n-dodecyl-3-O-n-octyl-2-O-2',3'-dihydroxypropylglycerol, 1-O-n-tetradecyl-3-O-methyl-2-O-2',3'-dihydroxypropylglycerol, 1-O-n-hexadecyl-3-O-methyl-2-O-2',3'-dihydroxypropylglycerol, 1-O-n-octadecyl-3-O-methyl-2O-2',3'-dihydroxypropylglycerol, 1-O-n-octadecenyl-3-O-methyl-2-O-2',3'-dihydroxypropylglycerol, 1-O-n-octadecenyl-3-O-n-butyl-2-O-2',3'-dihydroxypropylglycerol, 1-O-methyl-branched isostearyl-3-O-methyl-2-O-2',3'-dihydroxypropylglycerol, 1-0-methyl-branched isostearyl-3-0-n-butyl-2-0-2',3'-dihydroxypropylglycerol, and 1-0-methyl-branched isostearyl-3-0-n-octyl-2-0-2',3'-dihydroxypropylglycerol. The ether derivatives of glycerol or polyglycerol with these alcohols have extremely low toxicity in $LD_{50}$ of 5000 mg/kg or more.

The percutaneous absorption accelerator of the present invention is prepared using the ether derivative of glycerol or polyglycerol with alcohols as it is, or by dissolving, dispersing or suspending the ether derivative of glycerol or polyglycerol with alcohols in a suitable solvent such as water, ethanol, propylene glycol, triacetin, or the like. Further, the percutaneous absorption accelerator of the present invention may be formulated, if necessary, with known compounds having a percutaneously absorbing property, for example, dimethylsulfoxide, dimethylacetamide, dimethylformamide, N,N-diethyl-m-toluamide, azacycloalkan-2-one derivatives, such as 1-dodecylazacycloheptan-2-one, esters of alcohols and carboxylic acids, such as isopropyl myristate, isopropyl palmitate, diethyl sebacate, and diisopropyl adipate, crotonyl-N-ethyl-o-toluidine, and the like.

The percutaneous absorbent preparation of the present invention may be formulated by incorporating various pharmaceutically effective components with the percutaneous absorption accelerator. The percutaneous absorption accelerator can be advantageously used for many preparations of topical agents which are expected to exhibit the pharmacological effect upon application to skin, hair, nails, and the like to be absorbed for example, from a liquid spraying agent, a lotion, an ointment, a cream, a gel, a sol, an aerosol, a cataplasm, a plaster, a tape preparation, and the like.

Further, in a transmucosal administration, the percutaneous absorbent preparation of the present invention is prepared using the above-mentioned transmucosal absorption accelerator either as it is, or, by formulating the same in various forms of preparations for transmucosal administration, for example, suppositories for rectal and vaginal administration, an ointment, a soft gelatin capsule, a buccal tablet, a perlingual tablet, a nose drop, or a spraying agent for nasal mucous membrane or buccal mucous membrane, and, if necessary, further adding desired carriers, vehicles, etc. for preparations and making preparations in a conventional manner. In addition, the preparation for transmucosal absorbing activity may contain, for example, ether type non-ionic surfactants, enamine derivatives of phenylglycine, N-acylcollagen peptides, sodium salts of medium chain fatty acids, saponins, and so forth.

It is preferred that the percutaneous absorption accelerator of the present invention be formulated, as the effective component, in an amount of 0.001 to 10% by weight, particularly 0.1 to 8% by weight, into the preparation for percutaneous administration, based on the total amount of the preparation, as an aid for percutaneous absorption. Further, in the case of using the percutaneous absorption as the base for percutaneous absorption, it is also possible to formulate the same in an amount of 10% by weight or more.

Examples in which pharmaceutical effects increase by the utilization of the percutaneous absorbent preparation of the present invention as topical agents include steroid anti-inflammatory agents, such as prednisolone, and dexamethason, non-steroid anti-inflammatory agents, such as indomethacin, fulfenamic acid, and mefenamic acid, anti-histamic agents, such a tripernamine, insaibenzyl, chlorpheniramine, diphenhydramine, and promethazine; sulfa agents, such as sulfamonomethoxine, and sulfamethizole; and antibiotics, such as penecillan, cephalosporin, erythromycin, tetracyclin, chloramphenicol, and streptomycin; anti-fungal agents, such as napthiomate, and clotrimazole; anti-malignant tumor agents, such as 5-fluorouracil, cyclophosphamide, busulfan, and actinomycin; analgesics, such as morphine, codeine, nalorphine, pentazocine, aspirin, acetanilide, and aminopyrine; preparations of prostaglandins; hypnotics and tranquilizers, such as barbital, and thiopental; psychotropic agents, such as chlorpromazine, reserpine, and chlordiazepoxide; anti-epileptic agents; anti-Parkinson's syndrome agents, such as chlorzoxazone, and revodopa; cardiotonic agents, such as digitoxin, and digoxin; anti-arrhythmic agents, such as procainamide hydrochloride, and propranolol hydrochloride; anti-angina pectoris agents, such as dipyridamole, and amyl nitrite; anti-hypertension agents, such as reserpine, and guanethidine sulfate; UV inhibitors, such as p-aminobenzoate esters; agents for preventing the formation of melanine, such as hydroquinone, vitamin C esters, and p-hydroxycinnamate; PUVA treating agents against psoriasis, such as 8-methoxypsoralen; vitamins, such as vitamin A, estradiol, and methyltestosterone; diagnostics; allergens for patch test; vermicides, insecticides; moisturizers; keratin softening agents; hair dyes; and the like, but are not exhaustive thereof.

Further, the percutaneous absorbent preparation for the topical agent of the present invention is also effective for many drugs, agricultural chemicals, growth hormones, etc. for which pharmacological effects are expected by applying the same to animals, insects, plants, and so on to be absorbed therein.

Examples in which pharmaceutical effects increase by the utilization of the transmucosal absorption of the present invention include pharmacologically active polysaccharide substances such as heparin, dextran sulfate, pentosan sulfate (heparinoid), chondroitin sulfate and salts thereof, glucoamylase inhibitor; peptide type anti-tumor substances, such as bleomycin, neocarzinostan, and L-asparginase; enzyme preparations, such as trypsin, chemotrypsin, bromelain, papain, protenase, peroxidase, nagase, proctase, serratiopeptidase, seaprose, lysozyme, plasmin, urokinase, cytochrome C, hyaluronidase, fibrinolysine, thrombin, callidin, callikrein, plasmin, glucose oxidase, B-galactosidase, fytin, desoxyribonuclease, choline esterase, pronase, and pancreatin; peptide hormones, such as calcitonin, parathormone, relaxin, insulin, glucagon, prolactin, adrenocorticotropin (ACTH), gonaotropic hormone, thyrotropin (TSH), growth hormone (BGH), luteinizing hormone (LH), follicle-stimulating hormone (FSH), oxytocin, vasopressin, anti-diuretic hormone, coherin, melanocyte-stimulating hormone (MSH), gastrin, tetragastrin, pentagastrin, secretin, pancreozymin, cholecystokinin, Substance P, gonadotropin (HCG), and vasopressin; inhibitors for peptide hormone releasing factors, such as adrenocorticotropic hormone releasing factor (ACTH-RH), follicle-stimulating hormone releasing factor (FSH-RH), growth hormone releasing factor (GH-IH), luteinizing hormone releasing factor (LH-RH), prolactin releasing factor (PR-RH), prolactin inhibiting factor (PR-IH), and thyroid-stimulating hormone releasing factor (TSH-RH); polynucleotides, such as polyribonucleotide, complex of polyinocinic acid and cytidylic acid, complex of polyadenylic acid and polyuridilic acid, and polydeoxyribonucleotide; insulin secretion-activating protein (IAP), pancreas-basic trypsin inhibitor, antipain hydrochloride, chymostatin A, elastatinal, pepstatin A, polylysine, polyornithine, polyethylenimine, and polyvinylamine; steroid anti-inflammatory agents, such as prednisolone, and dexamethason; non-steroid anti-inflammatory agents, such as indomethacin, fulfenamic acid, and mefenamic acid; anti-histamic agents, such triperenamine, insaibenzyl, chlorpheniramine, diphenhydramine, and promethazine; sulfa agents, such as sulfamonomethoxine, and sulfamethizole; antibiotics, such as penicillin, cephalosporin, erythromycin, tetracyclin, chloramphenicol, and streptomycin; anti-malignant tumor agents, such as 5-fluororacil, cyclophosphamide, bulsulfan, and actinomycin; analgesics, such as morphine, codeine, nalophine, pentazocine, aspirin, acetanilide, and aminopyrine; preparations of prostaglandine; hypnotics and tranquilizers, such as barbital, and thiopental; psychotropic agents, such as chlorpromazine, reserpine, and chlordiazepoxide; anti-epileptic agents; anti-Parkinson's syndrome agents, such as chlorzoxazone, and revodopa; cardiotonic agents, such as digitoxin, and digoxin; anti-arrhythmic agents, such as procainamide hydrochloride, and propranolol hydrochloride; anti-angina pectoris agents, such as dipyridamole, and amyl nitrite; and anti-hypertension agents, such as reserpine, and guanethidine sulfate.

In the present percutaneous absorbent preparation, such a pharmaceutically effective component may be incorporated in a pharmaceutically effective amount according to the particular object to which the preparation is to be applied.

In the ether derivative used in the present invention, the structure can be appropriately chosen to control the balance between a hydrophilic property and an oleophilic property so that it is possible to prepare the ether derivative in any base having either a hydrophilic or oleophilic property. As a result, the ether derivative having a high solubility for various pharmaceutically effective components can be chosen according to the present invention. It is thus possible to design topical agents having good handling and high percutaneous absorption by dissolving difficultly soluble pharmaceutically effective components in hydrophilic bases in a high concentration.

BRIEF DESCRIPTION OF DRAWING

FIG. 1 shows a change in blood concentration of salicylic acid when the aspirin suppository of the present invention and the control aspirin suppository containing no transmucosal absorption accelerator were administered to rabbits.

ological saline for the above-mentioned 1-O-n-octyl-3-O-methyl-2-O-2',3'-dihydroxypropylglycerol was used. The results are shown in Table 2.

TABLE 2

| | Concentration of Insulin in Serum ($\mu$U/ml) | | | | | | |
|---|---|---|---|---|---|---|---|
| | 0 | 20 mins. | 40 mins. | 60 mins. | 90 mins. | 120 mins. | 180 mins. |
| Control | 5 | 8 | 12 | 12 | 12 | 14 | 14 |
| This Invention | 7 | 261 | 227 | 95 | 78 | 31 | 28 |

PREFERRED EMBODIMENTS

Next, the present invention will be described with reference to the examples below but it is not deemed to be limited only to these examples.

TEST EXAMPLE 1

Japanese white male rabbits weighing about 2.5 kg, fasted for 24 hours, were fixed at the back, and each of solutions shown in Table 1 was administered to the rectum of about 2.5 cm from the anus using a tube. Cannule was inserted into the femoral vein of the hind leg to collect about 0.2 ml each of blood in every fixed time interval. Blood sugar level was measured using destrostick. Change in blood sugar level was determined with the passage of time, as the blood sugar level prior to administration being rendered 100%. The results are shown in Table 1.

EXAMPLE 1

Topical agents containing indometacin shown below were prepared and percutaneous absorption was examined with the topical agents. The results are shown in Table 3.

Preparation

Preparation 1 of the present invention:

An ointment obtained by incorporating 3 g of 1-O-n-dodecyl-3-O-methyl-2-O-2',3'-dihydroxypropylglycerol into 97 g of a commercially available gel-like topical agent containing 1 wt % of indomethacin, Inteban ointment (made by Sumitomo Chemical Industry Co., Ltd.).

Preparation 2 of the present invention:

An ointment obtained by incorporating 3 g of 1-O-

TABLE 1

| Specimen | | Rate of Change in Blood Sugar Level before Administration (%) | | | | | |
|---|---|---|---|---|---|---|---|
| | | 15 mins. | 30 mins. | 45 mins. | 60 mins. | 90 mins. | 120 mins. |
| Control: | | | | | | | |
| Physiological saline | 0.75 g | | | | | | |
| Ethanol | 0.25 g | +10.2 | +12.5 | +11.2 | +11.2 | +12.2 | +18.0 |
| Insulin | 10/kg | | | | | | |
| 25% Ethanol solution | | +5.0 | +12.9 | +11.5 | +4.8 | +1.5 | +2.7 |
| 1-O—n-Dodecyl-3-O—methyl-2-O—2',3'-dihydroxypropylglycerol | 1 g | +6.5 | +10.2 | +9.8 | +9.5 | +9.5 | +10.2 |
| This Invention | | | | | | | |
| Physiological saline | 0.70 g | | | | | | |
| Ethanol | 0.25 g | | | | | | |
| Insulin | 10/kg | −13.4 | −18.6 | −25.2 | −27.6 | −25.8 | −22.4 |
| 1-O—n-Dodecyl-3-O—methyl-2-O—2',3'-dihydroxypropylglycerol | 0.05 g | | | | | | |
| Physiological saline | 0.65 g | | | | | | |
| Ethanol | 0.25 g | | | | | | |
| Insulin | 10/kg | −19.2 | −28.9 | −32.7 | −28.0 | −19.5 | −18.2 |
| 1-O—n-Dodecyl-3-O—methyl-2-O—2',3'-dihydroxypropylglycerol | 0.1 g | | | | | | |
| Physiological saline | 0.65 g | | | | | | |
| Ethanol | 0.25 g | | | | | | |
| Insulin | 10/kg | −17.8 | −18.3 | −24.5 | −28.6 | −21.9 | −19.8 |
| 1-O—Methyl-branched isostearyl-3-O—methyl-2-O—2',3'-dihydroxypropylglycerol | 0.1 g | | | | | | |

TEST EXAMPLE 2

To a mixture of 1.4 g of 1-O-n-octyl-3-O-methyl-2-O-2',3'-dihydroxypropylglycerol and 4.5 g of ethanol was added a 17 U/ml insulin solution in physiological saline and, the mixture was made 10 g in total to prepare a preparation for nasal spraying. The preparation was administered to the nasal cavity of male rabbits, weighing about 2.5 kg, fasted for 24 hours and fixed at the back, at a dose of 1 U/rabbit. Insulin in serum was quantitatively determined by enzyme immunoassay. For control, a preparation obtained by supplementing physimethyl-branched isostearyl-3-O-methyl-2-O-2',3'-dihydroxypropylglycerol into 97 g of a commercially available gel-like topical agent containing 1 wt % of indomethacin, Inteban ointment (made by Sumitomo Chemical Industry Co., Ltd.).

Preparation 3 of the present invention:

An ointment obtained by incorporating 3 g of 1-O-methyl-branched isostearyl-3-O-n-butyl-2-O-2',3'-dihydroxypropylglycerol into 97 g of a commercially available gel-like topical agent containing 1 wt % of indomethacin, Inteban ointment (made by Sumitomo Chemical Industry Co., Ltd.).

Preparation 4 of the present invention:

An ointment obtained by incorporating 3 g of 1-O-n-octyl-3-O-methyl-2-O-2',3'-dihydroxypropylglycerol into 97 g of a commercially available gel-like topical agent containing 1 wt % of indomethacin, Inteban ointment (made by Sumitomo Chemical Industry Co., Ltd.).

Preparation 5 of the present invention:

A liquid topical agent obtained by adding purified water to a mixture of 1 g of indomethacin, 14 g of 1-O-n-dodecyl-3-O-methyl-2-O-2',3'-dihydroxypropylglycerol and 45 g of ethanol to make 100 g.

Preparation 6 of the present invention:

A liquid topical agent obtained by adding purified water to a mixture of 1 g of indomethacin, 14 g of 1-O-methyl-branched isostearyl-3-O-methyl-2-O-2',3'-dihydroxypropylglycerol and 45 g of ethanol to make 100 g.

Preparation 7 of the present invention:

A liquid topical agent obtained by adding purified water to a mixture of 1 g of indomethacin, 14 g of 1-O-methyl-branched isostearyl-3-O-n-butyl-2-O-2',3'-dihydroxypropylglycerol and 45 g of ethanol to make 100 g.

Preparation 8 of the present invention:

A liquid topical agent obtained by adding purified water to a mixture of 1 g of indomethacin, 14 g of 1-O-n-octyl-3-O-methyl-2-O-2',3'-dihydroxypropylglycerol and 45 g of ethanol to make 100 g.

Comparative preparation 1

A commercially available gel-like topical agent containing 1 wt % of indomethacin, Inteban® ointment (made by Sumitomo Chemical Industry, Co., Ltd.).

Comparative preparation 2

A liquid topical agent obtained by adding purified water to a mixture of 1 g of indomethacin, 14 g of N,N-diethyl-m-toluamide and 45 g of ethanol to make 100 g.

Comparative preparation 3

A liquid topical agent obtained by adding purified water to a mixture of 1 g of indomethacin, 14 g of dimethylsulfoxide and 45 g of ethanol to make 100 g.

METHOD

Test of percutaneous absorption of indomethacin:

Seven (7) Japanese white female rabbits weighing about 3 kg were used as one group. The topical agents of the present invention and the comparative preparations were applied onto the normal abdominal skin (10 cm × 14 cm) of the rabbits in each group, from which the body hair was cut, respectively, at a dose corresponding to 20 mg of indomethacin. Blood was collected from the vein of the ear after 4, 10 and 20 hours and, blood concentration of indomethacin was measured.

TABLE 3

| Preparation | | Maximum Concentration in Serum (Cmax; ng/ml) |
|---|---|---|
| This invention | 1 | 540 |
| " | 2 | 510 |
| " | 3 | 500 |
| " | 4 | 420 |
| Comparative Preparation | 1 | 95 |
| This invention | 5 | 1900 |
| " | 6 | 1750 |
| " | 7 | 1550 |
| " | 8 | 1230 |
| Comparative Preparation | 2 | 190 |
| " | 3 | 150 |

As is clear from the results described above, topical agents 1 to 8 of the present invention all showed extremely high percutaneous absorption of indomethacin as compared to the comparative preparations. In particular, the topical agent of the present invention obtained by formulating 1-O-n-dodecyl-3-O-methyl-2-O-2',3'-dihydroxypropylglycerol as a percutaneous absorption accelerator showed extremely high percutaneous absorption of indomethacin.

EXAMPLE 2

With respect to the topical agents of the present invention, the pharmacological effect was examined according to the inhibition of carrageenin caused edema on the the paw of the rat. The results are shown in Table 4.

METHOD:

Wistar male 10 rats, weighing about 110 g, were used as one group. The volume of the right rear paw of the rats in each group was previously measured using a branched glass container. A 1% carrageenin aqueous solution was subcutaneously injected to the right rear paw sole in a dose of 0.125 ml. Immediately thereafter 0.3 g of indomethacin topical agents were applied to the skin of the right rear paw sole. In the control group, carrageenin alone was injected. Then, the volume of the rear paw was measured every 90 minutes, which was continued until 6 hours after. The rate of edema and the inhibition rate of edema were calculated as described below.

$$\frac{\text{rate of edema (\%)}}{100} = \frac{\text{volume of paw after injection}}{\text{volume of paw before injection}} - 1$$

$$\frac{\text{Inhibition rate of edema (\%)}}{100} =$$

$$1 - \frac{\text{rate of edema in the treated group}}{\text{rate of edema in the control group}}$$

TABLE 4

| Preparation | | Inhibition Rate of Edema (%) | | | |
|---|---|---|---|---|---|
| | | 1.5 hr | 3.0 hrs | 4.5 hrs | 6.0 hrs |
| This invention | 5 | 52.6 | 52.7 | 53.7 | 56.0 |
| " | 8 | 23.7 | 37.4 | 40.8 | 50.3 |
| Comparative Preparation | 1 | 10.5 | 3.9 | 3.5 | 2.0 |

As is clear from the results described above, the topical agents of the present invention showed an extremely high rate of preventing the edema caused by carrageenin due to the pharmacological effect of indomethacin, as compared to the comparative preparation. In particular, the topical agent obtained by formulating 1-O-n-dodecyl-3-O-methyl-2-O-2',3'-dihydroxypropylglycerol as a percutaneous absorption accelerator showed an extremely high pharmacological effect of indomethacin.

EXAMPLE 3

A topical agent containing mefenamic acid shown below was prepared and the percutaneous absorption was tested. The results are shown in Table 5.

Preparation 9 of the present invention:

Mefenamic acid, 1 g, was incorporated in a mixture of 10 g of propylene glycol, 5 g of 1-O-n-dodecyl-3-O-methyl-2-O-2',3'-dihydroxypropylglycerol and 30 g of ethanol. The mixture was added to a swollen mixture of 1 g of "HIVISWAKO-104" (made by Wako Pure Chemical Industries, Ltd., carboxymethyl polymer) in 20 g of purified water. After the mixture was homogeneously mixed, 3 g of 2% ammonia water was added thereto while stirring and, purified water was further added thereto to make 100 g to obtain a gel ointment.

Comparative preparation 4

Mefenamic acid, 1 g, was incorporated in a mixture of 15 g of propylene glycol and 30 g of ethanol. The mixture was added to a swollen mixture of 1 g of "HIVISWAKO-104" (made by Wako Pure Chemical Industries, Ltd., carboxymethyl polymer) in 20 g of purified water. After the mixture was homogeneously mixed, 3 g of 2% ammonia water was added thereto while stirring and, purified water was further added thereto to make 100 g to obtain a gel ointment.

METHOD:

Test for percutaneous absorption of mefenamic acid:

Seven (7) Japanese white female rabbits weighing about 3 kg were used as one group. The topical agents of the present invention and the comparative preparations were applied onto the normal abdominal skin (10 cm × 14 cm) of the rabbits in each group, from which the body hair was cut, respectively, at a dose corresponding to 50 mg of mefenamic acid. Blood was collected from the vein of the ear after 4, 10 and 20 hours and, blood concentration of mefenamic acid was measured.

TABLE 5

| Preparation | Concentration of Mefenamic Acid in Serum (C; μg/ml) | | |
|---|---|---|---|
| | 4 hrs | 10 hrs | 20 hrs |
| This invention 9 | 4.9 | 5.1 | 4.7 |
| Comparative Preparation | 1.8 | 1.1 | 0.4 |

As is clear from the results described above, the topical agent of the present invention showed extremely high percutaneous absorption of mefenamic acid, as compared to the comparative preparation.

EXAMPLE 4

Cataplasms shown below were prepared and, the percutaneous absorption of methyl salicylate was tested. The results are shown in Table 6.

Preparation:

Preparation 10 of the present invention:

To 10 parts (weight basis, hereafter the same) of gelatin were added 35 parts of water. The mixture was warmed to 70° C. to dissolve gelatin therein. To this solution were added 12 parts of titanium oxide, 10 parts of glycerol, 10 parts of sorbitol and 10 parts of 1-O-n-dodecyl-3-O-methyl-2-O-2',3'-dihydroxypropylglycerol. Then, 5 parts of self-cross linkable sodium polyacrylate (prepared in accordance with Example 1 of Published Examined Japanese Patent Application 30710/79) and 5 parts of sodium carboxymethyl cellulose were added to the mixture. Further 3 parts of a drug (drug mixture obtained by formulating 1-methanol, d-camphor and methyl salicylate in a weight ratio of 5:1:4) were added thereto and the mixture was kneaded to obtain a cataplasm paste composition. The composition was coated on a lint sheet. A polypropylene film was applied to the paste surface, which was cut into an appropriate size to obtain a cataplasm.

Preparation 11 of the present invention:

A cataplasm similar to Preparation 10 of the present invention was prepared by formulating 10 parts of 1-O-methylbranched isostearyl-3-O-methyl-2-O-2',3'-dihydroxypropylglycerol instead of 1-O-n-dodecyl-3-O-methyl-2-O-2',3'-dihydroxypropylglycerol in Preparation 10 of the present invention, 10 parts of glycerol and 10 parts of sorbitol.

Comparative preparation 5

A cataplasm similar to Preparation 10 of the present invention was obtained except that 15 parts of glycerol and 15 parts of sorbitol were used in place of 10 parts of glycerol and 10 parts of 1-O-n-dodecyl-3-O-methyl-2-O-2',3'-dihydroxypropylglycerol.

METHOD:

Test for percutaneous absorption of methyl salicylate:

Seven (7) Japanese white female rabbits weighing about 3 kg were used as one group. Each sheet of the cataplasms of the present invention and the comparative preparation, in which 1.2 wt. % of methyl salicylate was formulated, were applied to the normal abdominal skin (10 cm × 14 cm) of the rabbits in each group, from which the body hair was cut, respectively. Blood was collected from the vein of the femur after 3, 6, 10, 20 and 30 hours and, blood concentration of methyl salicylate was measured.

TABLE 6

| Preparation | Maximum Concentration in Serum (Cmax; μg/ml) | Reaching Time (Tmax; hr) |
|---|---|---|
| This invention | 10 | 47 | 10 |
| " | 11 | 41 | 10 |
| Comparative Preparation | 5 | 14 | 6 |

As is clear from the results above, the cataplasms of the present invention all showed extremely high percutaneous absorption of methyl salicylate, as compared to the cataplasm for comparison. In particular, the cataplasm of the present invention obtained by formulating 1-O-n-dodecyl-3-O-methyl-2-O-2',3'-dihydroxypropylglycerol as the percutaneous absorption accelerator showed extremely high percutaneous absorption of methyl salicylate.

EXAMPLE 5

Topical agents containing naphthiomate shown below were prepared and, the percutaneous absorption was tested. The results are shown in Table 7.

Preparation:

Preparation 12 of the present invention:

A mixture of 1 g of naphthiomate, 5 g of 1-O-n-dodecyl-3-O-methyl-2-O-2',3'-dihydroxypropylglycerol, 14 g of glycerol triacetate 30 g of methyl ethyl ketone and 50 g of ethanol was made a liquid topical agent.

Comparative preparation 6

A mixture of 1 g of naphthiomate, 19 g of glycerol triacetate 30 g of methyl ethyl ketone and 50 g of ethanol was made a liquid topical agent.

METHOD:

Test for percutaneous absorption of naphthiomate:

Wistar-strain male 10 rats, weighing about 150 g, were used as 1 group. The topical agent was applied to the normal back skin (5 cm × 4 cm) of the rats of each group, from which the body hair was cut, in a dose corresponding to 2 mg of naphthiomate. Blood was collected from the abdominal main artery after 10 hours and, blood concentration of naphthiomate was measured.

TABLE 7

| Preparation | | Concentration of naphthiomate in serum (C; ng/ml) |
| --- | --- | --- |
| This invention | 12 | 29.5 |
| Comparative Preparation | 6 | 9.3 |

As is clear from the results described above, the topical agent prepared in the example showed extremely high percutaneous absorption of naphthiomate, as compared to the comparative example.

EXAMPLE 6

Aspirin Suppository:

(1) Pharmacopeial aspirin: 1 g
(2) 1-O-n-Dodecyl-3-O-methyl-2-O-2',3'-dihydroxypropylglycerol: 0.5 g
(3) Homotex (made by Kao Soap Co., Ltd., medium chain fatty acid triglyceride): 8.5 g (1) to (3) were thoroughly agitated and mixed and, 1 g each of the mixture was filled up in a soft gelatin capsule to prepare an aspirin suppository.

The aspirin suppository of Example 6 was administered to male rabbits weighing about 3 kg and, change in blood concentration of salicylic acid was measured. For control, the following was used.

Control: suppository containing 100 mg of pharmacopeial aspirin in Homotex as a base.

The results are shown in FIG. 1.

EXAMPLE 7

Indometacin Suppository:

(1) Pharmacopeial indometacin: 1.5 g
(2) 1-O-Methyl-branched isostearyl-3-methyl-2-O-2',3'-dihydroxypropylglycerol: 0.5 g
(3) Homotex (supra): 8.0 g (1) to (3) were thoroughly agitated and mixed and, 1 g each of the mixture was filled up in a soft gelatin capsule to prepare an indometacin suppository.

EXAMPLE 8

In a manner similar to Example 6, an aspirin suppository was prepared using 1-O-n-octyl-3-O-methyl-2-O-2',3'-dihydroxypropylglycerol.

EXAMPLE 9

In a manner similar to Example 7, an indomethacin suppository was prepared using 1-O-n-dodecyl-3-O-methyl2-O-2',3'-dihydroxypropylglycerol.

EXAMPLE 10

Insulin Suppository:

(1) Solution of 100 IU of insulin in 0.5 ml of a 6% aqueous acetic acid solution: 0.5 g
(2) 1-O-n-Dodecyl-3-O-methyl-2-O-2',3'-dihydroxypropylglycerol: 0.5 g
(3) Homotex: 9.0 g After (1) to (3) were thoroughly agitated to disperse, 1 g each of the dispersion was filled up in a soft gelatin capsule to prepare an insulin suppository.

EXAMPLE 11

Insulin Spraying Agent for Nasal Use:

(1) Solution of 1000 IU of insulin in 2.0 ml of a 6% aqueous acetic acid solution: 2 g
(2) 1-Methyl-branched isostearyl-3-O-methyl- 2-O-2'3-dihydroxypropylglycerol: 2 g
(3) Ethanol: 6 g
(4) Physiological saline solution: 90 g (1) to (4) were thoroughly mixed, and, the mixture was filled up in a pump sprayer to make an insulin spraying agent for nasal use.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A percutaneous absorbent preparation for transdermal or transmucosal absorption of a pharmaceutically active substance, comprising:

an effective amount of indomethacin; and
an absorption accelerator selected from the group consisting of 1-O-n-decylglycerol, 1-O-n-octyl-3-O-2',3'-dihydroxypropylglycerol, 1-O-n-dodecyl-3-O-2',3'-dihydroxypropylglycerol, 1-O-n-tetradecyl-3-O-2',3'-dihydroxypropylglycerol, 1-O-n-hexadecyl-3-O-2',3'-dihydroxypropylglycerol, 1-O-n-octadecyl-3-O-2',3'-dihydroxypropylglycerol, 1-O-n-octadecenyl-3-O-2',3'-dihydroxypropylglycerol, 1-O-methyl-branched isostearyl-3-O-2',3'-dihydroxypropylglycerol, 1-O-n-octyl-2-O-methyl-3-O-2',3'-dihydroxypropylglycerol, 1-O-n-dodecyl-2-O-methyl-3-O-2',3'-dihydroxypropylglycerol, 1O-n-dodecyl-2-O-n-butyl-3-O-2',3'-dihydroxypropylglycerol, 1-O-n-dodecyl-2-O-n-octyl-3-O-2',3'-dihydroxypropylglycerol, 1-O-n-tetradecyl-2O-methyl-3O-2',3'-dihydroxypropylglycerol, 1-O-n-hexadecyl-2-O-methyl- 3-O-2',3'-dihydroxypropylglycerol, 1-O-n-octadecyl-2-O-methyl-3-O-2',3'-dihydroxypropylglycerol, 1-O-n-octadecenyl-2-O-methyl-3-O-2',3'-dihydroxypropylglycerol, 1-O-n-octadecenyl-2-O-n-butyl-3-O-2',3'-dihydroxypropyl-glycerol, 1-O-methyl-branched isostearyl-2-O-methyl-3-O-2',3'-dihydroxypropylglycerol, 1-O-methyl-branched isostearyl-2-O-n-octyl-3-O-2',3'-dihydroxypropylglycerol; 1O-n-octyl-3-O-methyl-2-O-2',3'-dihydroxypropylglycerol, 1-O-n-dodecyl-3-O-methyl-2-O-2',3'dihydroxypropylglycerol, 1-O-n-dodecyl-3-O-n-butyl-2-O-2',3'-dihydroxypropylglycerol, 1-O-n-dodecyl-3-O-n-octyl-2-O-2',3'-dihydroxypropylglycerol, 1-O-n-tetradecyl-3-O-methyl-2-O-2',3'-dihydroxypropylglycerol, 1-O-n-hexadecyl-3-O-methyl-2-O-2',3'-dihydroxypropylglycerol, 1-O-n-octadecyl-3-O-methyl-2-O-2',3'-dihydroxypropylglycerol, 1-O-n-octadecenyl-3-O-methyl-2-O-2',3'-dihydroxypropylglycerol, 1-O-n-octadecenyl-3-O-n-butyl-2-O-2',3'-dihydroxypropyl-glycerol, 1-O-methylbranched isostearyl-3-O-methyl-2-O-2′,3′-dihydroxypropylglycerol, 1-O-methyl-branched isostearyl-3-O-n-butyl-2-O-2′,3′-dihydroxypropylglycerol, and 1-O-methyl-branched isostearyl-3-O-n-octyl-2-O-2′,3′-dihydroxypropylglycerol.

2. The preparation of claim 1, wherein said accelerator is present in an amount of from 0.001 to 10% by weight of said preparation.

3. The preparation of claim 1, which further contains at least one member selected from the group consisting of ether type non-ionic surfactants, enamine derivatives of phenylglycine, N-acylcollagen peptides, and saponins.

4. The preparation of claim 1, which is in the form of a liquid, a lotion, an ointment, a cream, a gel, a sol, an aerosol, a cataplasm, a plaster, or a tape preparation.

5. A method for transdermal or transmucosal absorption of which indomethacin comprises administering an effective amount of the percutaneous absorbent preparation of claim 1 to the skin or a mucous membrane of a subject.

6. The preparation of claim 4, which is in the form of an ointment comprising (a) one member selected from the group consisting of 1-O-n-dodecyl-3-O-methyl-2-O-2′,3′-dihydroxypropylglycerol, 1-O-methyl-branched isostearyl-3-O-methyl-2-O-2′,3′-dihydroxypropylglycerol, 1-O-methyl-branched isostearyl-3-O-n-butyl-2-O-2′,3′-dihydroxypropylglycerol, and 1-O-n-octyl-3-O-methyl-2-O-2′,3′-dihydroxypropylglycerol; and (b) a topical agent containing 1 wt % of indomethacin.

7. The preparation of claim 4, which is in the form of a liquid topical agent comprising (a) one member selected from the group consisting of 1-O-n-dodecyl-3-O-methyl-2-O-2′,3′-dihydroxypropylglycerol, 1-O-methyl-branched isostearyl-3-O-methyl-2-O-2′,3′-dihydroxypropylglycerol, 1-O-methyl-branched isostearyl-3-O-n-butyl-2-O-2′,3′-dihydroxypropylglycerol, and 1-O-n-octyl-3-O-methyl-2-O-2′,3′-dihydroxypropylglycerol; (b) indomethacin; (c) ethanol; and (d) water.

8. The preparation of claim 1, wherein said accelerator is selected from the group consisting of 1-O-n-dodecyl-3-O-methyl-2-O-2′,3′-dihydroxypropylglycerol, 1-O-methyl-branched isostearyl-3-O-methyl-2-O-2′,3′-dihydroxypropylglycerol, 1-O-methyl-branched isostearyl-3-O-n-butyl-2-O-2′,3′-dihydroxypropylglycerol, and 1-O-n-octyl-3-O-methyl-2-O-2′,3′-dihydroxypropylglycerol.

* * * * *